United States Patent
Flohr et al.

(10) Patent No.: US 11,058,370 B2
(45) Date of Patent: Jul. 13, 2021

(54) INDIVIDUALLY ADJUSTED GENERATION OF VIRTUAL IMAGE DATA ON THE BASIS OF MULTI-ENERGY X-RAY IMAGING

(71) Applicant: Siemens Healthcare GmbH, Erlangen (DE)

(72) Inventors: Thomas Flohr, Uehlfeld (DE); Bernhard Schmidt, Fuerth (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/704,638

(22) Filed: Dec. 5, 2019

(65) Prior Publication Data
US 2020/0187872 A1    Jun. 18, 2020

(30) Foreign Application Priority Data
Dec. 13, 2018    (DE) .......................... 102018221691.6

(51) Int. Cl.
*A61B 6/03* (2006.01)
*A61B 6/00* (2006.01)
*G06T 11/00* (2006.01)

(52) U.S. Cl.
CPC .............. *A61B 6/032* (2013.01); *A61B 6/482* (2013.01); *A61B 6/504* (2013.01); *A61B 6/5205* (2013.01);
(Continued)

(58) Field of Classification Search
CPC ............ A61B 6/03; A61B 6/482; A61B 6/504
See application file for complete search history.

(56) References Cited

U.S. PATENT DOCUMENTS

2007/0255135 A1* 11/2007 Kalafut .................. A61B 5/026
                                                                     600/431
2009/0257549 A1* 10/2009 Heismann ............. G06T 11/005
                                                                     378/4
(Continued)

FOREIGN PATENT DOCUMENTS

DE    102011083727 A1    4/2013
DE    102014203463 B3    7/2015
(Continued)

OTHER PUBLICATIONS

Yu Lifeng et al.; "Dual-Energy CT-Based Monochromatic Imaging"; American journal of Roentgenology; Jahrgang 199; No. 5; pp. 9-15; 2012.
(Continued)

*Primary Examiner* — Hugh Maupin
(74) *Attorney, Agent, or Firm* — Harness, Dickey & Pierce, P.L.C.

(57) ABSTRACT

An X-ray imaging method is for generating image data of a field of view of an object to be examined. In the method, firstly an individual imaging protocol is determined for imaging of the object to be examined. Furthermore, first X-ray projection measurement data with a first X-ray energy spectrum and at least one set of second contrast medium-influenced X-ray projection measurement data with a second X-ray energy spectrum, are acquired from the field of view. A third X-ray energy spectrum with a third mean energy is then determined on the basis of the determined individual imaging protocol. Subsequently, preferably pseudo-monoenergetic image data, associated with the third X-ray energy spectrum, is reconstructed on the basis of the acquired first and at least second X-ray projection measurement data as well as the determined imaging protocol. An image data-
(Continued)

generating device is also described. A computerized tomography system is described, moreover.

21 Claims, 3 Drawing Sheets

(52) U.S. Cl.
CPC ....... *G06T 11/005* (2013.01); *G06T 2211/404* (2013.01)

(56) References Cited

U.S. PATENT DOCUMENTS

| | | | | |
|---|---|---|---|---|
| 2010/0303196 | A1* | 12/2010 | Zou | A61B 6/542 378/5 |
| 2013/0083989 | A1 | 4/2013 | Flohr et al. | |
| 2014/0005533 | A1* | 1/2014 | Grasruck | A61B 6/481 600/425 |
| 2015/0238160 | A1 | 8/2015 | Flohr et al. | |
| 2017/0245816 | A1 | 8/2017 | Flohr et al. | |
| 2017/0301082 | A1 | 10/2017 | Allmendinger et al. | |

FOREIGN PATENT DOCUMENTS

| | | |
|---|---|---|
| DE | 102015223601 A1 | 6/2017 |
| DE | 102016203257 A1 | 8/2017 |
| WO | WO 2020006352 A1 | 1/2020 |

OTHER PUBLICATIONS

German Office Action dated Mar. 11, 2020.
Alvarez, R. E. et al. "Energy-selective reconstructions in X-ray computerised tomography" Physics in Medicine & Biology, vol. 21, No. 5, pp. 733-744, Sep. 1976 // DOI: 10.1068/0031-9155/21/5/002.
Grant, K.L., et.al.: "Assessment of an Advanced Image-Based Technique to Calculate Virtual Monoenergetic Computed Tomographic Images From a Dual-Energy Examination to Improve Contrast-To-Noise Ratio in Examinations Using Iodinated Contrast Media", in: Investigative Radiology: 2014.

* cited by examiner

US 11,058,370 B2

INDIVIDUALLY ADJUSTED GENERATION OF VIRTUAL IMAGE DATA ON THE BASIS OF MULTI-ENERGY X-RAY IMAGING

PRIORITY STATEMENT

The present application hereby claims priority under 35 U.S.C. § 119 to German patent application number DE 102018221691.6 filed Dec. 13, 2018, the entire contents of each of which are hereby incorporated herein by reference.

FIELD

Embodiments of the invention generally relate to an X-ray imaging method for the generation of image data; an image data-generating device; and a computerized tomography system.

BACKGROUND

With the aid of modern imaging methods, two- or three-dimensional image data is often generated which can be used for the visualization of an imaged examination object and also for further applications, moreover.

In many cases the imaging methods are based on the detection of X-ray radiation, with what is known as projection measurement data being generated. For example, projection measurement data can be acquired with the aid of a computerized tomography system (CT system). In CT systems a combination of X-ray source arranged on a gantry and an X-ray detector arranged opposite conventionally revolves around a measuring space in which the examination object (which is usually referred to in the following, without limiting the generality, as the patient). The center of rotation (also called "isocenter") coincides with what is known as a system axis z in this case. The patient is irradiated with X-ray radiation from the X-ray source on one or more revolution(s), with projection measurement data or X-ray projection measurement data being acquired with the aid of the opposing X-ray detector.

The generated projection measurement data is dependent in particular on the design of the X-ray detector. X-ray detectors usually have a plurality of detection units which are usually arranged in the form of a regular pixel array. For X-ray radiation that strikes the detection units, the detection units in each case generate a detection signal, which is analyzed at particular instants in respect of intensity and spectral distribution of the X-ray radiation in order to draw conclusions about the examination object and generate projection measurement data.

In CT examinations the tube voltage is frequently adjusted to patient parameters, such as their height and stature, and to the type of planned examination. For example, native imaging without contrast medium or an examination of a parenchymal organ, such as the liver, can be carried out with contrast medium or a CT angiography method with contrast medium.

The radiation dose can be reduced, above all in examinations with contrast medium containing iodine, owing to the use of lower tube voltages (such as 80 kV or 100 kV) instead of the conventional 120 kV due to the higher iodine contrast and the higher contrast-noise ratio (CNR) for iodine. The contrast-noise ratio, which is normally achieved with a voltage of 120 kV, is achieved with a lower radiation dose with a lower tube voltage. The extent to which the radiation dose can be reduced depends on the type of examination: with CT angiographic examinations, in which only the contrast-noise ratio is relevant, the radiation dose can be reduced much more than for example with portal venous examinations of the liver in which a particular image noise must not be exceeded either. In order to automatically take into account these correlations that are complex for the user, there are programs for automatically adjusting the tube voltage, such as "CAREkV", which automatically determine the optimal tube voltage respectively, depending on the patient and as a function of the type of planned examination and the technical possibilities of the CT equipment. Alternatively, similar methods can also be used for the reduction of the contrast medium dose or for a combination of radiation dose reduction and adjustment of the quantity of contrast medium.

One drawback with an adjustment of the tube voltage to the patient geometry and the planned examination is the high tube power, which is necessary with low tube voltages in order to achieve an adequate contrast-noise ratio, in particular in the case of patients of a larger build. CT imaging at low tube voltages therefore requires specially developed and cost intensive X-ray tubes with correspondingly higher power. In addition, the CT data set is defined by the choice of tube voltage during the acquisition of CT data. The visual representation cannot be changed retrospectively. In particular, image contrasts (for example between organ regions, which absorb contrast medium, and their surroundings) defined by the choice of tube voltage can no longer be changed retrospectively.

SUMMARY

The inventors have discovered that there is the problem in an X-ray imaging method and a corresponding image data-generating device, to enable good image quality with optimally lower contamination for the patient, be it due to X-ray radiation or contrast medium.

Embodiments of the application are directed to an X-ray imaging method for the generation of image data, an image data-generating device and a computerized tomography system.

In an embodiment, an X-ray imaging method is for reconstructing pseudo-monoenergetic image data of a field of view of an object to be examined, the X-ray imaging method comprising:

determining an individual imaging protocol for imaging of the object to be examined;

acquiring first X-ray projection measurement data from the field of view, with a first X-ray energy spectrum with a first mean energy, and acquiring at least second X-ray projection measurement data from the field of view, with a second X-ray energy spectrum with a second mean energy;

automatically determining a third X-ray energy spectrum with a third mean energy, based upon the individual imaging protocol determined; and reconstructing pseudo-monoenergetic image data, associated with the third X-ray energy spectrum with the third mean energy, based upon the individual imaging protocol determined, the first X-ray projection measurement data acquired and the at least second X-ray projection measurement data acquired In an embodiment, an image data-generating device comprises:

a determining unit to determine an individual imaging protocol for imaging an object to be examined;

a control unit to control one or more X-ray sources of a CT system to generate X-ray beams having a first X-ray energy spectrum with a first mean energy value, and to generate X-ray beams having a second X-ray energy spectrum and with a second mean energy value;

a projection measurement data acquisition unit to acquire first X-ray projection measurement data with the first X-ray energy spectrum from a field of view of the object to be examined and to acquire at least second projection measurement data with the second X-ray energy spectrum from the field of view of the object to be examined;

an energy spectrum-determining unit to automatically determine a third X-ray energy spectrum with a third mean energy value, based upon the individual imaging protocol determined; and an image data reconstruction unit for reconstructing pseudo-monoenergetic image data, associated with the third X-ray energy spectrum, based upon the first X-ray projection measurement data acquired first and the at least second X-ray projection measurement data acquired.

An inventive computerized tomography system of at least one embodiment includes the image data-generating device of an embodiment.

At least one embodiment on the invention is directed to a non-transitory computer program product storing a computer program, directly loadable into a memory unit of an image data-generating device, including program segments to carry out the method of an embodiment when the computer program is run in the image data-generating device.

At least one embodiment on the invention is directed to a non-transitory computer readable medium, storing program segments, readable and executable by a processing unit of an image data-generating device, to carry out the method of an embodiment when the program segments are executed by the processing unit of the image data-generating device.

At least one embodiment on the invention is directed to an image data-generating device, comprising:

at least one processor to determine an individual imaging protocol for imaging an object to be examined;

control one or more X-ray sources of a CT system to generate X-ray beams having a first X-ray energy spectrum with a first mean energy value, and to generate X-ray beams having a second X-ray energy spectrum and with a second mean energy value;

acquire first X-ray projection measurement data with the first X-ray energy spectrum from a field of view of the object to be examined and to acquire at least second projection measurement data with the second X-ray energy spectrum from the field of view of the object to be examined;

automatically determine a third X-ray energy spectrum with a third mean energy value, based upon the individual imaging protocol determined; and reconstruct pseudo-monoenergetic image data, associated with the third X-ray energy spectrum, based upon the first X-ray projection measurement data acquired first and the at least second X-ray projection measurement data acquired.

BRIEF DESCRIPTION OF THE DRAWINGS

The invention will be explained once again in more detail below using example embodiments with reference to the accompanying figures. In the drawings.

DETAILED DESCRIPTION OF THE EXAMPLE EMBODIMENTS

Figure 1:
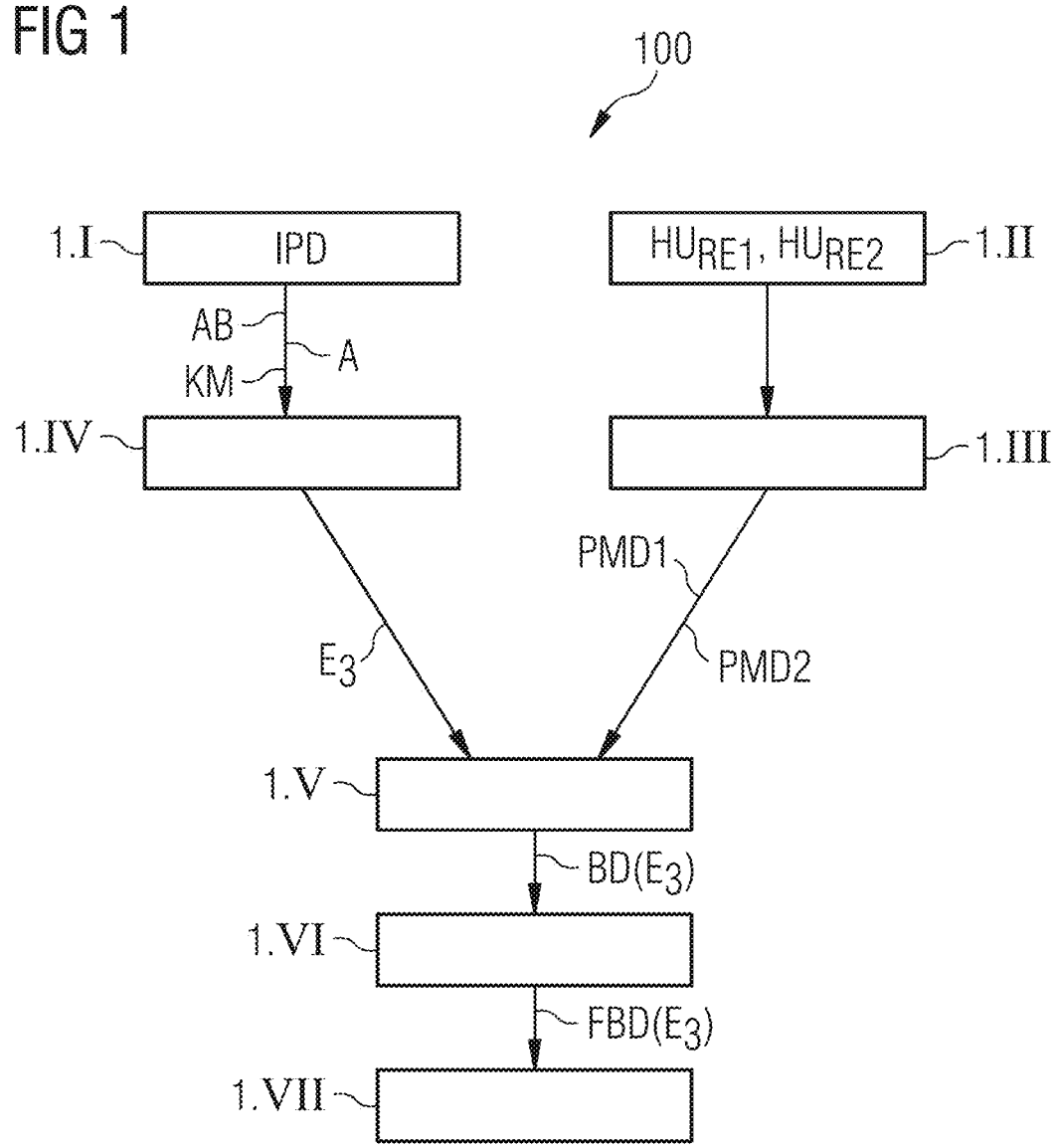
FIG. 1 shows a flowchart, which illustrates a method for the generation of image data of a field of view of an object to be examined.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In an embodiment, an X-ray imaging method, preferably a CT X-ray imaging method, for the generation of image data from a field of view of an object to be examined, firstly includes determining an individual imaging protocol for imaging of the object to be examined. The examination object and information specifying the imaging process are considered when determining the imaging protocol. Furthermore, first X-ray projection measurement data with a first X-ray energy spectrum and at least second X-ray projection measurement data with a second X-ray energy spectrum is acquired from the field of view on the basis of the individual imaging protocol.

For acquiring the X-ray projection measurement data, for example what is known as a dual-energy measuring method can be used, in which X-ray radiation with different X-ray energy spectra is emitted in the direction of a region to be examined, is partially absorbed by it and the transmitted portion of the X-ray radiation is then detected by different detectors. The detectors do not have to be spectral.

In the case of the dual source, a method in which two separate X-ray sources with different X-ray energies are used, or in the case of kV-switching, in which the electrical voltage of the X-ray source is changed over between different values, conventional detectors are used even today. In this case acquisition takes place with different spectra.

Alternatively, the spectral data can also be acquired with a spectrally resolving detector. In this case acquisition with just one spectrum is then sufficient. Energy separation is achieved in this case at the detector (in contrast to the methods above in which different spectra are used). In general it is also possible, however, to combine the above methods with a spectral detector.

During the course of evaluating the acquired measurement data a third X-ray energy spectrum with a third mean energy, preferably a single third energy value, is automatically determined on the basis of the individual imaging protocol. This process can take place, for example, analogously to known calculations for adjusting X-ray tube voltages, it being possible to define certain parameters of the imaging process, such as the contrast-noise ratio, the quantity of contrast medium and the X-ray dose. For example, the third mean energy can be determined analogously to known calculations for adjusting X-ray tube voltages to the patient habitus (height and weight) and to the planned examination (CT examination without contrast medium, CT examination of a parenchymal organ with contrast medium, CT angiography). Preferably pseudo-monoenergetic image data, which is associated with the third X-ray energy spectrum with the third mean energy, preferably a single third energy value, is then reconstructed on the basis of the acquired first and at least second X-ray projection measurement data as well as the determined image reconstruction parameters.

Where a third X-ray energy spectrum with a third mean energy is mentioned below, this should particularly preferably also always include the specific embodiment in which pseudo-monoenergetic X-ray images are generated according to known material breakdown methods on the basis of a single energy. The "mean" energy then corresponds to this single energy value.

Therefore, on the basis of the acquired multispectral X-ray projection measurement data an X-ray image with an X-ray spectrum or a third mean energy, preferably a single energy value, is calculated as a type of mixed image, in the case of the single energy value also referred to as a pseudo-monoenergetic mixed image. Advantageously, this third mean energy or the single third energy value is selected as a function of the individual imaging protocol such that particular predetermined parameters of the imaging process and of the result of the imaging are satisfied. This can include, for example, the specification that the image contrast/noise ratio of the image acquisition with this third energy is particularly advantageous.

The inventive image data-generating device of at least one embodiment has a determining unit for the determination of an individual imaging protocol for imaging of the object to be examined. A determining unit of this kind can comprise, for example, an input interface or a data acquisition interface with which data associated with the examination object, for example a patient, either by an operator or from a database, and also data about the type of imaging to be used is received. This data is then used by the determining unit to create an individual imaging protocol.

Furthermore, the inventive image data-generating device of at least one embodiment comprises a control unit for controlling one or more X-ray source(s) of a CT system in such a way that X-rays with a mean energy of a first X-ray radiation energy spectrum and a mean energy of a second X-ray radiation energy spectrum are generated.

Part of the inventive image data-generating device is, moreover, a control unit for controlling one or more X-ray source(s) of a CT system in such a way that X-ray beams with the first X-ray energy spectrum and the second X-ray energy spectrum are generated with a first and second mean energy respectively. The two energy values can be preset standard values.

The inventive image data-generating device of at least one embodiment comprises moreover a projection measurement data acquisition unit for the acquisition of first X-ray projection measurement data with the first X-ray energy spectrum and second X-ray projection measurement data with the second X-ray energy spectrum from a field of view of an examination object.

Furthermore, the inventive image data-generating device of at least one embodiment comprises an energy spectrum-determining unit for the automatic determination of a third energy spectrum on the basis of the individual imaging protocol determined by the determining unit.

Part of the inventive image data-generating device of at least one embodiment is also an image data reconstruction unit for the reconstruction of pseudo-monoenergetic image data, which is associated with the third X-ray energy spectrum, preferably the single third X-ray energy value, on the basis of the acquired first and at least second X-ray projection measurement data.

A method for the reconstruction or calculation of pseudo-monoenergetic image data is known from Alvarez R. E. and Macovski A. "Energy-selective reconstructions in x-ray computed tomography", Phys. Med. Biol. 21, 733-744 (1976), the entire contents of which are hereby incorporated herein by reference.

A particularly suitable method for the reconstruction or calculation of pseudo-monoenergetic image data is described in K. L. Grant et al. "Assessment of an Advanced Image-Based Technique to Calculate Virtual Monoenergetic Computed Tomographic Images From a Dual-Energy Examination to Improve Contrast-To-Noise Ratio in Examinations Using Iodinated Contrast Media", Investigative Radiology 2014; 00: 00-00), the entire contents of which are hereby incorporated herein by reference.

When generating pseudo-monoenergetic image data, the acquired projection measurement data is broken down in the raw data space or the image data reconstructed therefrom in the image data space. For example, when using an iodine contrast medium, breaking-down into an iodine/chalk component and into a water/soft tissue component occurs and then, with the aid of tabulated values for an X-ray energy value (keV value) chosen by the user, an attenuation value (HU value) for the respective voxel is calculated based on density values. The acquired first and/or second projection measurement data is preferably projection measurement data, which is generated in the presence of a contrast medium. For example, a water or a tissue component can be rendered particularly clearly visible with a contrast medium.

The inventive image data-generating device of at least one embodiment shares the advantages of the inventive X-ray imaging method of at least one embodiment.

The inventive computerized tomography system of at least one embodiment has an inventive image data-generating device of at least one embodiment. The inventive image data-generating device of at least one embodiment can in particular be part of a control device of the computerized tomography system. The inventive computerized tomography system shares the advantages of the inventive image data-generating device of at least one embodiment.

The fundamental components of the inventive image data-generating device of at least one embodiment can for the most part be configured in the form of software components. This relates in particular to the determining unit, the control unit, the energy spectrum-determining unit and the image data reconstruction unit. Basically, these components can also be implemented partly in the form of software-assisted hardware, for example FPGAs or the like, however, especially when particularly fast calculations are involved. Similarly, the necessary interfaces, for example when it is merely a matter of acquiring data from other software components, can be configured as software interfaces. However, they can also be configured as interfaces constructed in terms of hardware and which are controlled by appropriate software.

An implementation largely in terms of software has the advantage that even previously used image data-generating devices or control devices of computerized tomography systems can be easily retrofitted by way of a software update in order to operate inventively. In this regard the object is also achieved by a corresponding computer program product having a computer program, which can be loaded directly into a storage device of an inventive image data-generating device of at least one embodiment or a storage device of a control device of a computerized tomography system and comprises program segments in order to carry out all steps of at least one embodiment of the inventive method when the computer program is run in the image data-generating devices or by the control device of the computerized tomography system.

In addition to the computer program, a computer program product of at least one embodiment can optionally comprise additional components, such as documentation and/or additional components, also hardware components, such as hardware keys (dongles, etc.), in order to utilize the software.

At least one embodiment on the invention is directed to a computer-readable medium, for example a memory stick, a hard disk or another portable or permanently fitted data carrier, on which the program segments of the computer program, which can be read-in and executed by an arithmetic unit of the image data-generating device are stored, can be used for transportation to the storage device of the image data-generating device or control device of the computerized tomography system and/or for storage on the image data-generating device or control device of the computerized tomography system. The arithmetic unit can, for example, have one or more cooperating microprocessor(s) or the like for this purpose.

The claims and the following description each contain particularly advantageous embodiments and developments of the invention. In particular, the claims of one category can also be developed analogously to the dependent claims relating to a different category of claims. Furthermore, within the scope of the invention the various features of different example embodiments and claims can also be combined to form new example embodiments.

In one embodiment of the inventive X-ray imaging method a lower, compared to the first and the second energy value, third mean energy value is chosen. The choice of a lower third mean energy value enables an improved contrast-noise ratio of the image data reconstructed with this energy or alternatively with the same contrast-noise ratio, a lower X-ray dose on acquisition of the projection measurement data.

In an advantageous embodiment of the inventive X-ray imaging method the third mean energy value is chosen in such a way that, compared to an image representation with the first or second energy value, an improved contrast-noise ratio is achieved. Conventionally, a lower third mean energy value is chosen for this compared to the first and second mean energy values. An improved contrast-noise ratio of the reconstructed image data can be achieved with a constant X-ray dose.

For a noise reduction an algorithm for noise reduction can also be used when calculating the pseudo-monoenergetic image data, which algorithm is based, for example, on what is known as a frequency-split method. A method of this kind is, for example, the Mono+ method from Siemens.

In another embodiment of the inventive X-ray imaging method the imaging protocol comprises at least one of the following selectable parameters:
the patient geometry,
the type of planned examination,
a predetermined image quality,
a maximum radiation dose.

The patient geometry influences, for example, the necessary tube power for acquisition of the required projection measurement data, in particular with low tube voltages. In order to nevertheless achieve the advantages of low tube voltages, namely an improved contrast-noise ratio or a lower required X-ray dose, but keep the tube power within the scope of the technical possibilities of a CT imaging system, the acquisition itself is now advantageously carried out with higher X-ray voltages, for example a specified standard X-ray voltage, such as 120 keV, and the reconstruction with a lower energy is implemented via the detour of pseudo-monoenergetic image data.

The type of planned examination can, for example, be relevant as to how greatly a radiation dose can be reduced. In CT angiographic examinations, in which only the contrast-noise ratio is relevant, the radiation dose can be reduced much more than in portal venous examinations of the liver in which a particular image noise should not be exceeded either.

The type of planned examination can comprise one of the following types of examination:
acquisition of contrast-enhanced image data,
image acquisition without contrast medium,
an examination of a parenchymal organ with contrast medium, an examination using CT angiography.

In addition, other types of examination may be defined which profit from the calculation of a third energy: for example, image acquisition of an organ with metal implants (for example, artificial hip joint).

The chosen third mean energy value is dependent on the type of image acquisition. For example, for standard abdomen examinations, higher energy values are required than with image acquisition in the context of CT angiography.

Particularly in the case of image acquisitions of organs with metal implants (for example, artificial hip joint), image artifacts caused by the metal can be effectively reduced by the calculation of images with a third mean energy value, which is higher compared to an image representation with the first or second energy value.

It is especially beneficial to health if the third mean energy value is chosen in such a way that the radiation dose required during the acquisition can be reduced. This is conventionally the case with an optimally low energy value.

The third mean energy value can also be chosen in such a way that the contrast medium dose required during acquisition can be reduced. This effect too is produced with the choice of a lower third mean energy value. A lower contrast medium concentration also reduces the contamination of or the risks to the patient.

The third mean energy value is preferably automatically determined by an auto-keV algorithm, which is based on an auto-kV algorithm. Auto-kV algorithms are known in the prior art. The tube voltage can be automatically adjusted, for example with programs, which are known by the name of "CAREkV", depending on the patient and as a function of the planned examination and the technical parameters of the X-ray imaging equipment. Programs of this kind can also be used for the reduction of the contrast medium dose and for adjusting a reduced radiation dose and a reduced quantity of contrast medium. As already mentioned, in the prior art it is disadvantageous that tube powers required for low tube voltages, which are necessary to achieve an adequate contrast-noise ratio, in particular in the case of patients of a larger build, often cannot be attained as a result of technical limitations. Advantageously, the tube voltages used as standard are inventively not changed on acquisition of the projection measurement data as a function of individual parameters of the examination object and the type of examination, and instead a virtual third mean energy is automatically determined when generating monoenergetic image data with the aid of an auto-keV method, in which a suitable energy of a virtual X-ray spectrum of pseudo-monoenergetic image data is determined instead of a suitable tube voltage.

This procedure has the same positive effect as the choice of lower tube voltages but compared to the conventional procedure, it has the advantage that there are no limitations owing to the technical possibilities of the X-ray tubes.

With an auto-kV method, an image optimization variable is calculated in the background for all available tube voltages respectively. The image optimization variable depends on the planned type of examination. For example in CT angiographic examinations, the iodine-contrast-noise ratio achievable at a given radiation dose is the variable to be optimized; in CT examinations of a parenchymal organ, the contrast-noise ratio is optimized, wherein, at the same time, a specific image noise must not be exceeded.

In CT examinations without contrast medium on the other hand, the image noise is minimized. The value of the image optimization variable with a particular tube voltage depends on the patient habitus, in other words, for example their height, weight, and the X-ray attenuation thereof, which is known from an overview image (tomogram). With the auto-kV method, that tube voltage is accordingly chosen for the CT acquisition with which the image optimization variable achieves the best possible value for the desired type of examination with the given patient habitus. Whether this tube voltage can then actually be used conventionally depends on the current power limitations of the X-ray tube of the relevant CT equipment. If the tube voltage cannot be used, the next-higher possible tube voltage, for example, is used even if the image optimization variable does not then attain its best possible value.

With the auto-keV method, CT data relating to two energy values is acquired from the outset with one or two tube voltages which are high enough that the CT scan can be performed for the relevant patient habitus. The third mean energy of the image data set for display is then determined in a manner similar to the auto-kV method. For example, for all possible third mean energies (all possible keV values), an image optimization variable is determined whose value in the case of the single energy values depends on the type of examination and patient habitus. The auto-keV method accordingly chooses the third energy with which the image optimization variable attains the best possible value.

In a specific variant of the inventive X-ray imaging method, for the case that an acquisition takes place without contrast medium, an optimally high energy value is chosen as the third mean energy value. Advantageously, hardening artifacts and metal artifacts can be reduced in this procedure. Since no contrast medium is used in this case, the choice of a lower mean energy does not result in a better contrast-noise ratio either. Therefore, it is advantageous in this case to use a higher third mean energy value for the generation of pseudo-monoenergetic image data, with which said artifacts are reduced and therefore an improved image quality is achieved.

FIG. 1 shows a flowchart 100, which illustrates a CT imaging method with the aid of what is known as the dual-energy technique, in which contrast-enhanced image data is generated from a patient, according to one example embodiment of the invention.

In an imaging method with the aid of the dual-energy technique, two projection measurement data sets PMD1, PMD are acquired, which are each generated by X-ray beams with different X-ray energy spectra $R_{E1}$, $R_{E2}$ with different mean energies $E_1$, $E_2$. For the generation of the X-ray beams with different X-ray energy spectra $R_{E1}$, $R_{E2}$, for example two X-ray sources 15a, 15b (see FIG. 3) can be used, which emit X-ray beams with different X-ray energies $E_1$, $E_2$ or X-ray energy spectra $R_{E1}$, $R_{E2}$.

In the course of the imaging method, firstly individual protocol data IPD for an image acquisition of an object to be examined, in this case a patient O, is determined in step 1.I. The protocol data can comprise, for example, the dimensions A of the patient O and the type of imaging AB, in this case contrast medium-enhanced imaging in the form of angiography. The dimensions A can include, for example, the build of the patient, their height, BMI, body mass, a density distribution inside the body of the patient or other information.

Furthermore, information about the type of contrast medium KM administered in advance before the start of the imaging method is acquired. Different contrast media can comprise different X-ray absorption edges, also called X-ray edge for short. The situation of the X-ray edge relative to the energy E3 of a pseudo-monoenergetic X-ray image to be subsequently determined has an effect on the image contrast of the X-ray image, so knowledge of the energy value of the X-ray absorption edge of the contrast medium KM is crucial for the image quality of the X-ray image to be reconstructed with the aid of at least one embodiment of the inventive imaging method.

In step 1.II two different X-ray tubes then generate X-ray beams with high-energy first and second X-ray energy spectra $R_{E1}$, $R_{E2}$. These X-ray energy spectra $R_{E1}$, $R_{E2}$ are generated with the aid of high first and second tube voltages $HU_{RE1}$, $HU_{RE2}$. With the aid of the first and second tube voltages $HU_{RE1}$ and $HU_{RE2}$ the X-ray tubes are excited to generate X-ray radiation with predetermined first and second mean energies E1, E2. In particular when using iodine as the contrast medium, the first and second tube voltages $HU_{RE1}$, $HU_{RE2}$ are, for example, preferably 120 kV and 140 kV.

In step 1.III the X-ray beams generated by the two X-ray sources with different first and second X-ray spectra or X-ray energy spectra with high mean energies $E_1$, $E_2$ are detected by two X-ray detectors 16a, 16b (see FIG. 3) arranged opposite the respective X-ray sources. This imaging method, also known as the dual-energy method, is used in the method applied in FIG. 1 for generating first and second projection measurement data sets PMD1, PMD2, which are associated with the respective different X-ray energy spectra $R_{E1}$, $R_{E2}$.

In step 1.IV a lower energy value $E_3$ is then automatically determined on the basis of the individual imaging parameters A, KM, which value means an improved contrast-noise ratio can be expected. For an angiography method, for example, this energy value $E_3$ can lie at 50 keV and for a standard abdomen examination, at 70 keV. The calculation can be made by way of a determining method, which is based on an auto-kV algorithm, although virtual energies are accordingly calculated instead of tube voltages. Reference is therefore made to an auto-keV algorithm in this connection.

In step 1.V pseudo-monoenergetic image data $BD(E_3)$ is also reconstructed from the acquired X-ray projection measurement data PMD1, PMD2, the associated virtual X-ray energy of which has a low energy value $E_3$ compared to the mean energies $E_1$, $E_2$ of the first and second X-ray energy spectra.

In step 1.VI a filter procedure is then applied to the obtained monoenergetic image data $BD(E_3)$, with which procedure the image noise of the obtained pseudo-monoenergetic image data $BD(E_3)$ is reduced. A method of this kind is described, for example, in DE 10 2011 083 727 A1, the entire contents of which are hereby incorporated herein by reference into the present patent application. In current dual-source CT apparatuses, such as the SOMATOM Definition Flash, the filtered monoenergetic image data $FBD(E_3)$ thus obtained with low energies $E_3$ has a higher contrast-noise ratio than images that were obtained directly by single energy-acquisition methods with low tube voltages. Compared to single-energy image acquisitions, the contrast-noise ratio increases by 20-50% as a function of the size of the phantom and this can be converted directly into a corresponding reduction of the radiation dose.

In step 1.VII the filtered image data $FBD(E_3)$ is output, for example to a database or on an output screen.

In the CT imaging method, as has been described in connection with FIG. 1, an individually matched determination of a virtual X-ray spectrum takes place, which is adjusted to imaging parameters and patient parameters. The image representation generated thereby can be improved, compared to the image information acquired with standard energies $E_1$, $E_2$, in respect of different parameters. For example, an improved image contrast can be achieved and/or the required quantity of contrast medium reduced.

The required radiation dose can also be reduced below a predetermined amount. Instead of only adjusting the tube voltage of the X-ray source to low-energy values when calculating the image information, the individual imaging parameters are also considered, so an adjustment at the hardware level is not necessary.

Furthermore, the problem of limited X-ray tube power, in particular with low energies, may also be avoided since the adaption to the individual imaging parameters only occurs with the evaluation of the acquired projection measurement data PMD1, PMD2 and not during the course of preparation of an imaging process due to changes to setting parameters of the CT imaging system itself. Therefore a greater degree of freedom is achieved in the choice of energy of the virtual X-ray spectrum $RE_3$ that ultimately underlies an image representation, and this contributes to improved image quality.

Figure 2:
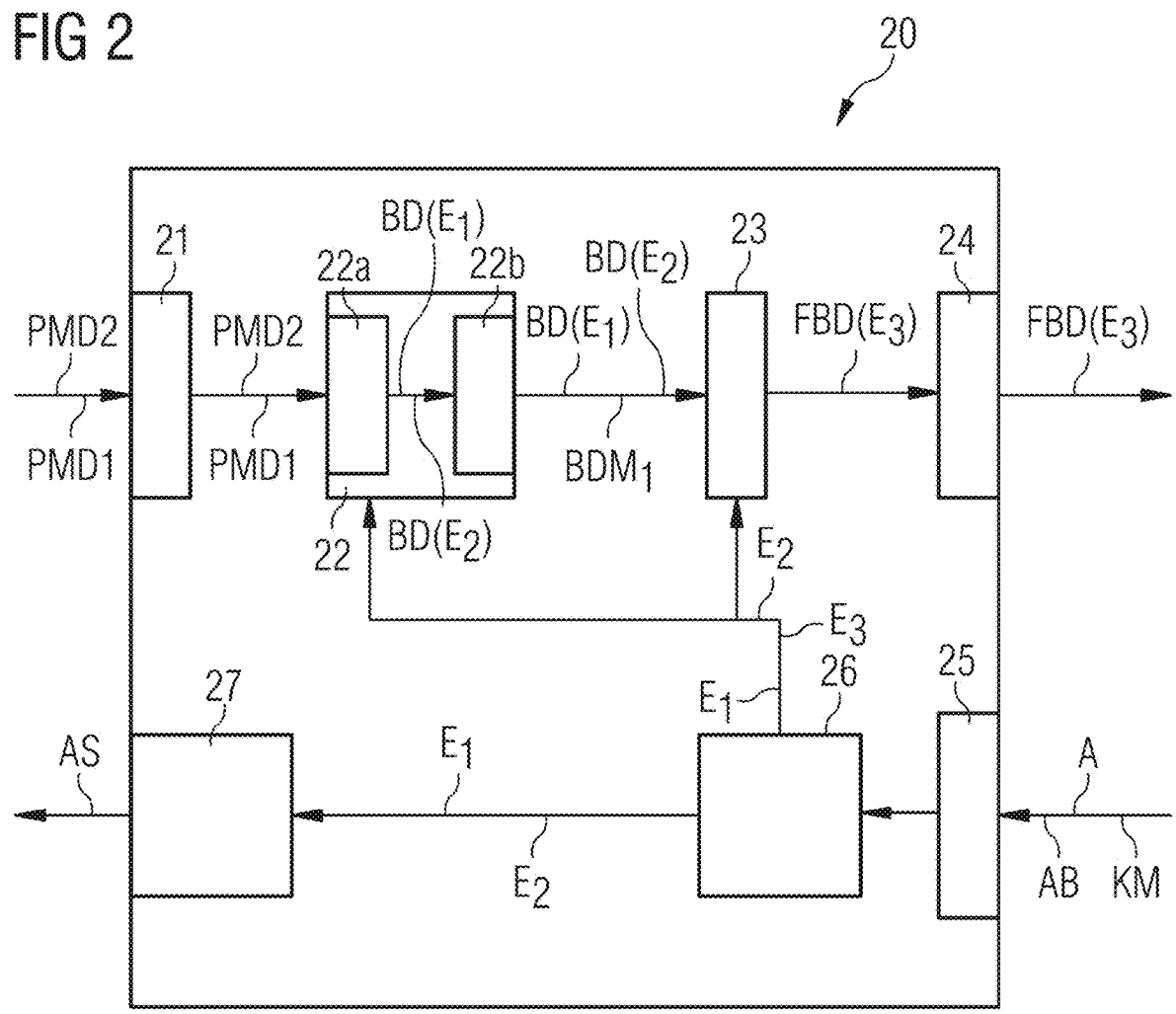
FIG. 2 shows a block diagram with which an image data-generating system according to one example embodiment of the invention is illustrated.

FIG. 2 schematically shows an image data-generating device 20 according to one example embodiment of the invention.

The image data-generating device 20 comprises an input interface 25, with which information, which provides details about the absorption behavior of a FOV of a patient to be examined, in particular dimension parameter values A, and information in respect of the type AB of imaging method used and of the contrast medium KM administered to the patient in advance before an imaging method, is acquired. The input interface 25 transfers the acquired data A, AB, KM to an energy spectrum-determining unit 26.

With the aid of an auto-keV algorithm and on the basis of preset values $E_1$, $E_2$ for mean energies $E_1$ of a first X-ray energy spectrum $R_{E1}$ and a second mean energy $E_2$ of a second X-ray energy spectrum $R_{E2}$ and the input data A, AB, KM, the energy spectrum-determining unit 26 determines a third X-ray energy value $E_3$, for which, with the aid of the image data-generating device 20, what is known as pseudo-monoenergetic image data $BD(E_3)$ is to be determined.

The energy value $E_3$ can be chosen in such a way, for example, that for a desired image contrast/noise ratio, a reduced required radiation dose is achieved during image acquisition. In other words, it is accordingly possible to use a lower radiation dose with the values of the first and second mean energies $E_1$, $E_2$ chosen as standard because the third mean energy $E_3$ is chosen to be lower accordingly.

On the basis of the first and second energy values $E_1$, $E_2$ a control unit 27 accordingly generates control signals AS, which are transferred to a control interface 34 (see FIG. 3) of the associated CT system. Furthermore, the determined values of the first and second mean energies $E_1$, $E_2$ and the third energy $E_3$ are transferred to a reconstruction unit 22 yet to be described and a filter unit 23 yet to be described.

The image data-generating device 20 shown in FIG. 2 also comprises a projection measurement data acquisition unit 21. The projection measurement data acquisition unit 21 is used for the acquisition of X-ray projection measurement data PMD1, PMD2 with different energy spectra $E_1$, $E_2$ from a field of view FOV of an examination object O during the actual imaging process or also from a database in which the X-ray projection measurement data PMD1, PMD2 has been stored. The X-ray projection measurement data PMD1, PMD2 is generated during the imaging process in that the field of view FOV is subject to X-ray beams with first and second X-ray energy spectra $R_{E1}$, $R_{E2}$ and the transmitted X-ray beams are detected by detectors (see detectors 16a, 16b in FIG. 3) that are separate from each other. The X-ray projection measurement data PMD1, PMD2 generated by the detectors generated and acquired by the projection measurement data acquisition unit 21 is then passed to an image data reconstruction unit 22, which reconstructs pseudo-monoenergetic image data $BD(E_3)$ therefrom.

The image data reconstruction unit 22 comprises a single image data reconstruction unit 22a. With the aid of the single image data reconstruction unit 22a, single images $BD(E_1)$, $BD(E_2)$ are firstly reconstructed for the first X-ray energy spectrum $R_{E1}$ and the second X-ray energy spectrum $R_{E1}$ or the associated first X-ray projection measurement data PMD1 and the second X-ray projection measurement data PMD2. These single images $BD(E_1)$, $BD(E_2)$ are then transferred to an image mixing unit 22b, which, on the basis of the single images $BD(E_1)$, $BD(E_2)$, generates a first pseudo-monoenergetic mixed image $BDM_1=BD(E_3)$ according to the following formula:

$$BD(E_3)=w(E_3) \cdot BD(E_1)+(1-w(E_3)) \cdot BD(E_2). \tag{1}$$

The composition $w(E_3)$ is a function of a virtual energy $E_3$. The pseudo-monoenergetic image data $BDM_1=BD(E_3)$ is associated with this third virtual X-ray energy $E_3$.

The generated mixed pseudo-monoenergetic image data $BDM_1$ is then transferred to a filter unit 23, which reduces the image noise in the generated mixed image data $BDM_1$. Filtering is achieved in that at least one further mixed image $BDM_2$ or, in the general case (m-1), additional mixed images $BDM_2 \ldots BDM_m$ is/are generated on the basis of the single images $BD(E_1)$, $BD(E_2)$ with coefficients $c_1$, $c_2$, which differ from the two coefficients $w(E_3)$ and $(1-w(E_3))$ and also among themselves in at least one coefficient. Filtered image data $FBD(E_3)$ is then generated according to:

$$FBD(E_3) = FBDM_1 = \sum_{j<=m} g_j(r) F_j BDM_j. \tag{2}$$

Here, $FBDM_1$ is the filtered first mixed image $BDM_1$. The scaling function $g_1(r)$ has the value 1 and the remaining scaling functions $g_j(r)$ are defined in such a way that at the location r, an image or an intensity value is produced which matches that of the first mixed image $BDM_1$, apart from the noise.

The filters $F_j$ are spectral filters and are defined as follows:

$$\sum_{j<=m} F_j = 1, \tag{3}$$

with the single spectral filter $F_j$ breaking down the mixed images in each case into frequency bands or energy components and a low pass filter corresponding to the first spectral filter $F_1$, which includes the frequency f=0 or the associated energy E=0 at full strength.

As already mentioned, a filter method of this kind is described in DE 10 2011 083 727 A1, the entire contents of which are hereby incorporated herein by reference. Filter methods for the reduction of the noise in X-ray images are also described in the applications with application numbers 10 2015 223 601.4 and in 10 2015 223 606.4 at the German Patent and Trademark Office, the entire contents of each of which are hereby incorporated herein by reference.

The filtered image data $FBD(E_3)$, largely freed of noise, is then transferred to an output interface 24, from which the filtered image data $FBD(E_3)$ is output, for example to a data storage unit (see FIG. 3, data storage unit 32) or transferred to a display unit on which is it depicted.

Figure 3:
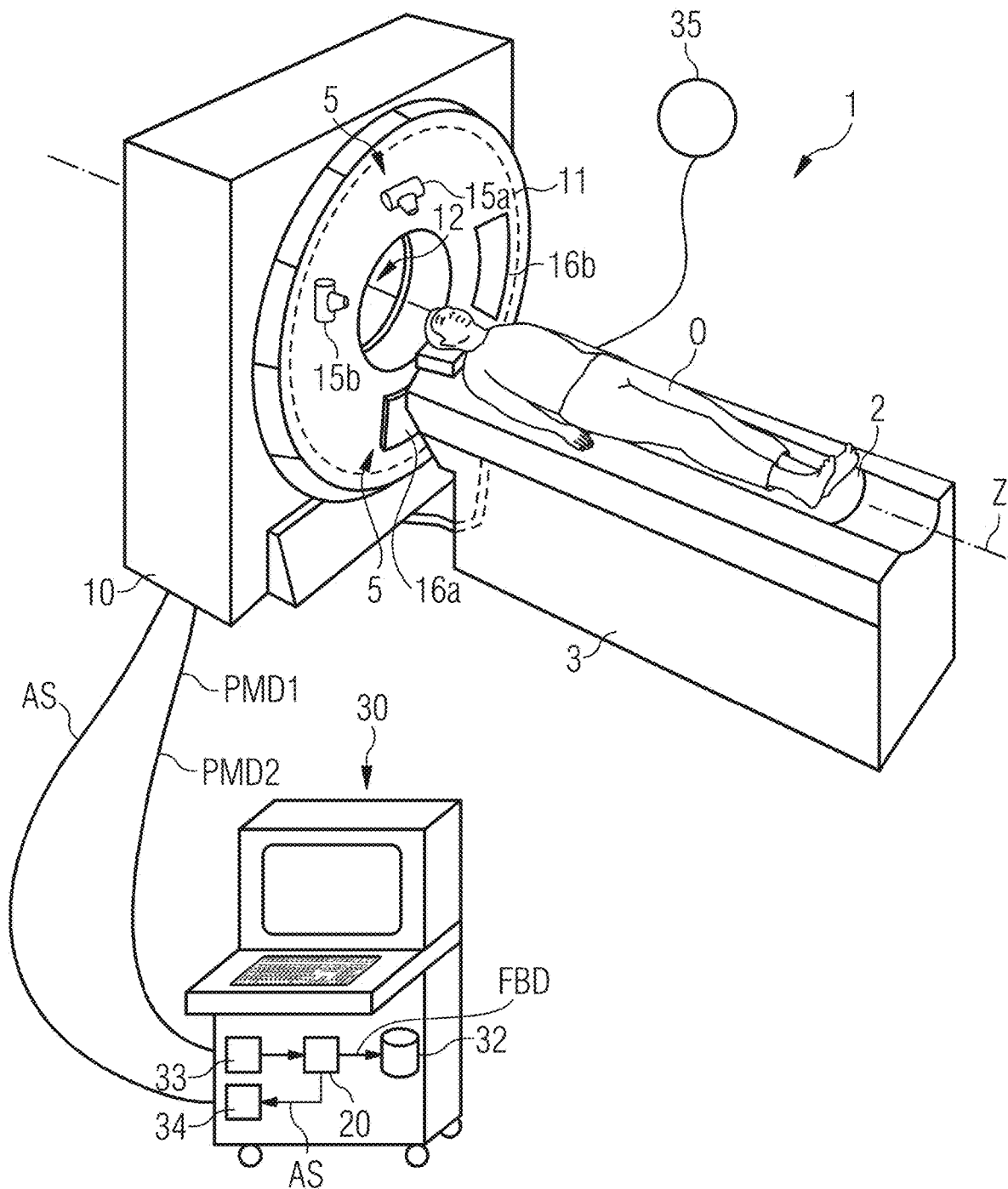
FIG. 3 shows a schematic representation of a computerized tomography systems according to one example embodiment of the invention.

FIG. 3 shows a computerized tomography system 1, which comprises the image data-generating device 20 shown in FIG. 2. The CT System 1, which is designed as a dual-energy CT system, is substantially composed of a conventional scanner 10, in which, on a gantry 11, a projection measurement data acquisition unit 5 having two detectors 16a, 16b and two X-ray sources 15a, 15b opposite the detectors 16a, 16b revolve around a measuring space 12. In front of the scanner 10 is a patient positioning device 3 or a patient couch 3, whose upper part 2, with a patient O situated thereon, can be pushed in the direction of the scanner 10 in order to move the patient O through the measuring space 12 relative to the detector system 16a, 16b. The scanner 10 and the patient couch 3 are controlled by a control device 30, from which acquisition control signals AS emanate via a conventional control interface 34 to conventionally control the entire system according to predefined measuring protocols. In the case of a spiral acquisition, a movement of the patient O along the z-direction, which corresponds to the system axis z longitudinally through the measuring space 12, and the simultaneous revolution of the X-ray sources 15a, 15b produces a helical path for the X-ray sources 15a, 15b relative to the patient O during the measurement. The detectors 16a, 16b run concurrently, always opposite the X-ray sources 15a, 15b, in order to detect projection measurement data PMD1, PMD2, which is then used for the reconstruction of volume and/or slice image data.

Similarly, a sequential measuring method can also be carried out in which a fixed position in the z-direction is approached and then during one revolution, a partial revolution or a plurality of revolutions the requisite projection measurement data PMD1, PMD2 is acquired at the relevant z-position in order to reconstruct a sectional image at this z-position or to reconstruct image data from the projection measurement data of a plurality of z-positions. At least one embodiment of the inventive method can basically also be used on other CT systems, for example having just one X-ray source or a detector forming a complete ring. For example, the inventive method may also be applied to a system having a patient couch that does not move and a gantry moved in the z-direction (what is known as a sliding gantry).

The projection measurement data PMD1, PMD2 (also called raw data below) acquired by the detectors 16a, 16b is transferred via a raw data interface 33 to the control device 30. This raw data is then processed further, optionally following suitable preparation in an image data-generating device 20, which in this example embodiment is implemented on a processor in the control device 30, in the form of software. On the basis of the raw data PMD1, PMD2 this image data-generating device 20 reconstructs pseudo-monoenergetic image data $FBD(E_3)$ with the aid of the inventive method. The exact construction of an image data-generating device 20 of this kind is shown in detail in FIG. 2.

The pseudo-monoenergetic image data $FBD(E_3)$ generated by the image data-generating device 20 is then stored in a storage device 32 of the control device 30 and/or conventionally output on the screen of the control device 30. It can also be fed via an interface (not shown in FIG. 3) into a network connected to the computerized tomography system 1, for example a radiological information system (RIS), and stored in a mass storage device that is accessible there or output as images on printers or filming stations connected there. The data can therefore be processed further in any desired manner and then be stored or output in any way. By way of the image data-generating device 20, suitable control parameters or control signals AS are then also determined on the basis of previously input data, in particular dimension parameter values A and information AB about the type imaging. The control signals AS are then transferred to said control interface 34. The units directly involved in imaging, such as the X-ray sources 15a, 15b, the detectors 16a, 16b, the patient couch 3 etc., are then controlled from there.

In addition, FIG. 3 also shows a contrast medium injection device 35 with which a contrast medium is injected in advance into the patient O, in other words before the start of the CT imaging method. The quantity of contrast medium used can be minimized with the aid of the inventive imaging method, so stress on the patient due to side effects of contrast media are likewise reduced.

The components of the image data-generating device 20 can be predominantly or completely implemented on a suitable processor in the form of software elements. In particular, the interfaces between these components can also be configured purely in terms of software. It is only necessary that it is possible to access appropriate storage areas in which the data can be suitably buffered and retrieved and updated again at any time.

In conclusion, reference is made once again to the fact that the above-described methods and devices are merely preferred example embodiments of the invention and that the invention can be varied by a person skilled in the art without departing from the scope of the invention insofar as it is specified by the claims. The method and the image data-generating device has therefore primarily been explained on the basis of a system for acquiring medical image data. The invention is not limited to an application in the medical sector, however, rather it can basically also be applied to the acquisition of images for other purposes. For the sake of completeness reference is also made to the fact that use of the indefinite article "a" or "an" does not preclude the relevant features from also being present several times. Similarly, the term "unit" does not preclude this from comprising a plurality of components, which can also be optionally also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An X-ray imaging method for reconstructing pseudo-monoenergetic image data of a field of view of an object, the X-ray imaging method comprising:
   determining an individual imaging protocol for imaging the object;
   acquiring first X-ray projection measurement data from the field of view using a first X-ray energy spectrum with a first mean energy value;
   acquiring at least second X-ray projection measurement data from the field of view using a second X-ray energy spectrum with a second mean energy value;
   automatically determining a third X-ray energy spectrum with a third mean energy value based upon the individual imaging protocol; and
   reconstructing pseudo-monoenergetic image data associated with the third X-ray energy spectrum with the third mean energy value, based on the individual imaging protocol, the first X-ray projection measurement data and at least the second X-ray projection measurement data.

2. The method of claim 1, wherein the third mean energy value is lower than the first mean energy value and the second mean energy value.

3. The method of claim 1, wherein the third mean energy value is chosen to improve contrast-noise ratio relative to an image representation based on the first mean energy value or the second mean energy value.

4. The method of claim 1, wherein the individual imaging protocol includes at least one of
   patient geometry,
   a type of planned examination,
   a quality, or
   a maximum radiation dose.

5. The method of claim 4, wherein the type of planned examination includes at least one of
   acquisition of contrast-enhanced image data,
   image acquisition without contrast medium,
   examination of a parenchymal organ with contrast medium, or CT angiography.

6. The method of claim 1, wherein the third mean energy value is chosen to reduce a radiation dose required during the acquiring first X-ray projection measurement data.

7. The method of claim 1, wherein the third mean energy value is chosen to reduce a contrast medium dose required during the acquiring of the first X-ray projection measurement data.

8. The method of claim 1, wherein the third mean energy value is automatically determined based on an auto-keV algorithm.

9. The method of claim 1, wherein, upon at least one of the acquiring first X-ray projection measurement data or the acquiring at least second X-ray projection measurement data being performed without contrast medium, an optimally high energy value is chosen as the third mean energy value.

10. An image data-generating device, comprising:
    a determining unit to determine an individual imaging protocol for imaging an object;
    a control unit to control one or more X-ray sources of a CT system to generate X-ray beams having a first X-ray energy spectrum with a first mean energy value, and to generate X-ray beams having a second X-ray energy spectrum with a second mean energy value;

a projection measurement data acquisition unit to acquire first X-ray projection measurement data with the first X-ray energy spectrum from a field of view of the object, and to acquire at least second X-ray projection measurement data with the second X-ray energy spectrum from the field of view of the object;

an energy spectrum-determining unit to automatically determine a third X-ray energy spectrum with a third mean energy value based on the individual imaging protocol; and an image data reconstruction unit to reconstruct pseudo-monoenergetic image data associated with the third X-ray energy spectrum, based on the first X-ray projection measurement data and at least the second X-ray projection measurement data.

11. A computerized tomography system comprising the image data-generating device of claim 10.

12. A non-transitory computer program product storing a computer program directly loadable into a memory of an image data-generating device, the computer program including program segments to carry out the method of claim 1 when the computer program is run in the image data-generating device.

13. A non-transitory computer readable medium storing program segments, which are readable and executable by a processing unit of an image data-generating device, to carry out the method of claim 1 when the program segments are executed by the processing unit of the image data-generating device.

14. The X-ray imaging method of claim 1, wherein the X-ray imaging method is a CT X-ray imaging method.

15. The X-ray imaging method of claim 1, wherein
the third mean energy value is a single third energy value; and
the reconstructing includes reconstructing the pseudo-monoenergetic image data associated with the third X-ray energy spectrum with the single third energy value.

16. The method of claim 15, wherein the single third energy value is chosen to reduce a radiation dose required during the acquiring first X-ray projection measurement data.

17. The method of claim 15, wherein the single third energy value is chosen to reduce a contrast medium dose required during the acquiring of the first X-ray projection measurement data.

18. The method of claim 15, wherein the single third energy value is automatically determined based on an auto-keV algorithm.

19. The method of claim 15, wherein, upon at least one of the acquiring first X-ray projection measurement data or the acquiring at least second X-ray projection measurement data being performed without contrast medium, an optimally high energy value is chosen as the single third energy value.

20. An image data-generating device, comprising:
at least one processor to
determine an individual imaging protocol for imaging an object;
control one or more X-ray sources of a CT system to generate X-ray beams having a first X-ray energy spectrum with a first mean energy value, and to generate X-ray beams having a second X-ray energy spectrum with a second mean energy value;
acquire first X-ray projection measurement data with the first X-ray energy spectrum from a field of view of the object;
acquire at least second X-ray projection measurement data with the second X-ray energy spectrum from the field of view of the object;
automatically determine a third X-ray energy spectrum with a third mean energy value based upon the individual imaging protocol; and
reconstruct pseudo-monoenergetic image data associated with the third X-ray energy spectrum, based on the first X-ray projection measurement data and at least the second X-ray projection measurement data.

21. A computerized tomography system, comprising:
the image data-generating device of claim 20; and
the one or more X-ray sources to generate the X-ray beams.

* * * * *